(12) United States Patent
Edoga et al.

(10) Patent No.: US 7,335,212 B2
(45) Date of Patent: Feb. 26, 2008

(54) MULTIPLE STAPLING DEVICE FOR NARROW BLOOD VESSELS

(75) Inventors: John K. Edoga, Morristown, NJ (US); Thierry Richard, Florham Park, NJ (US)

(73) Assignee: Edrich Vascular Devices, Inc., Morristown, NJ (US)

( * ) Notice: Subject to any disclaimer, the term of this patent is extended or adjusted under 35 U.S.C. 154(b) by 645 days.

(21) Appl. No.: 10/737,630

(22) Filed: Dec. 16, 2003

(65) Prior Publication Data

US 2004/0176786 A1    Sep. 9, 2004

Related U.S. Application Data

(60) Provisional application No. 60/433,687, filed on Dec. 16, 2002.

(51) Int. Cl.
- A61B 17/10 (2006.01)
- A61B 17/08 (2006.01)
- A61B 17/04 (2006.01)

(52) U.S. Cl. .................. 606/139; 606/153; 227/175.1; 227/178.1

(58) Field of Classification Search ................ 606/153, 606/142, 72, 75, 151, 157, 219; 227/175.1, 227/178.1, 179.1, 901
See application file for complete search history.

(56) References Cited

U.S. PATENT DOCUMENTS

| | | | |
|---|---|---|---|
| 3,388,847 A | 6/1968 | Kasulin et al. | |
| 3,552,626 A | 1/1971 | Astafiev et al. | |
| 4,006,747 A | 2/1977 | Kronenthal et al. | |
| 4,553,543 A | 11/1985 | Amarasinghe | |
| 4,573,468 A | 3/1986 | Conta et al. | |
| 4,595,007 A | 6/1986 | Mericle | |
| 4,693,249 A | 9/1987 | Schenck et al. | |
| 4,754,909 A | 7/1988 | Barker et al. | |
| 4,944,295 A | 7/1990 | Swathmey et al. | |
| 5,005,749 A | 4/1991 | Aranyi | |
| 5,258,008 A | 11/1993 | Wilk | |
| 5,275,322 A | 1/1994 | Brinkerhoff et al. | |
| 5,346,115 A * | 9/1994 | Perouse et al. | 227/179.1 |
| 5,366,462 A | 11/1994 | Kaster et al. | |
| 5,403,333 A | 4/1995 | Kaster et al. | |
| 5,453,454 A | 9/1995 | Alicke et al. | |
| 5,499,990 A | 3/1996 | Schulken et al. | |
| 5,533,661 A | 7/1996 | Main et al. | |

(Continued)

FOREIGN PATENT DOCUMENTS

EP    0 270 260 A1    10/1987

(Continued)

Primary Examiner—Anhtuan T. Nguyen
Assistant Examiner—Timothy J Neal
(74) Attorney, Agent, or Firm—Lerner, David, Littenberg, Krumholz & Mentlik, LLP

(57) ABSTRACT

A multiple stapling device for stapling a graft to a vessel. The device includes a body having a plurality of staple channels housing straight wire segments extending therethrough. A plurality of staple drivers, one in each of the staple channels is adapted to push the straight wire segments to form ring-shaped staples piercing the graft and the vessel. The multiple stapling device may also include one or more bolsters filling the annular space created by they ring-shaped staples. One such bolster may be formed, or otherwise connected to, the prosthesis.

14 Claims, 19 Drawing Sheets

U.S. PATENT DOCUMENTS

| | | | |
|---|---|---|---|
| 5,593,421 | A | 1/1997 | Bauer |
| 5,639,008 | A | 6/1997 | Gallagher et al. |
| 5,653,744 | A | 8/1997 | Khouri |
| 5,659,504 | A | 8/1997 | Bude et al. |
| 5,674,231 | A | 10/1997 | Green et al. |
| 5,707,380 | A | 1/1998 | Hinchliffe et al. |
| 5,817,113 | A | 10/1998 | Gifford, III et al. |
| 5,824,043 | A | 10/1998 | Cottone, Jr. |
| 5,915,616 | A | 6/1999 | Viola et al. |
| 5,951,576 | A | 9/1999 | Wakabayashi |
| 5,993,468 | A * | 11/1999 | Rygaard .................. 606/151 |
| 5,993,469 | A | 11/1999 | McKenzie et al. |
| 6,024,748 | A | 2/2000 | Manzo et al. |
| 6,146,393 | A * | 11/2000 | Wakabayashi ............ 606/153 |
| 6,171,321 | B1 * | 1/2001 | Gifford et al. ............ 606/153 |
| 6,203,553 | B1 | 3/2001 | Robertson et al. |
| 6,248,117 | B1 | 6/2001 | Blatter |
| 6,253,984 | B1 | 7/2001 | Heck et al. |
| 6,254,617 | B1 | 7/2001 | Spence et al. |
| 6,387,105 | B1 | 5/2002 | Gifford, III et al. |
| 6,391,039 | B1 | 5/2002 | Nicholas et al. |
| 6,402,008 | B1 | 6/2002 | Lucas |
| 6,440,146 | B2 | 8/2002 | Nicholas et al. |
| 2001/0004697 | A1 * | 6/2001 | Blatter et al. ............ 606/153 |
| 2002/0019642 | A1 | 2/2002 | Milliman et al. |
| 2002/0025243 | A1 | 2/2002 | Heck |
| 2002/0128669 | A1 | 9/2002 | Field et al. |

FOREIGN PATENT DOCUMENTS

| | | | |
|---|---|---|---|
| GB | 2 025 236 A | 1/1980 | |

* cited by examiner

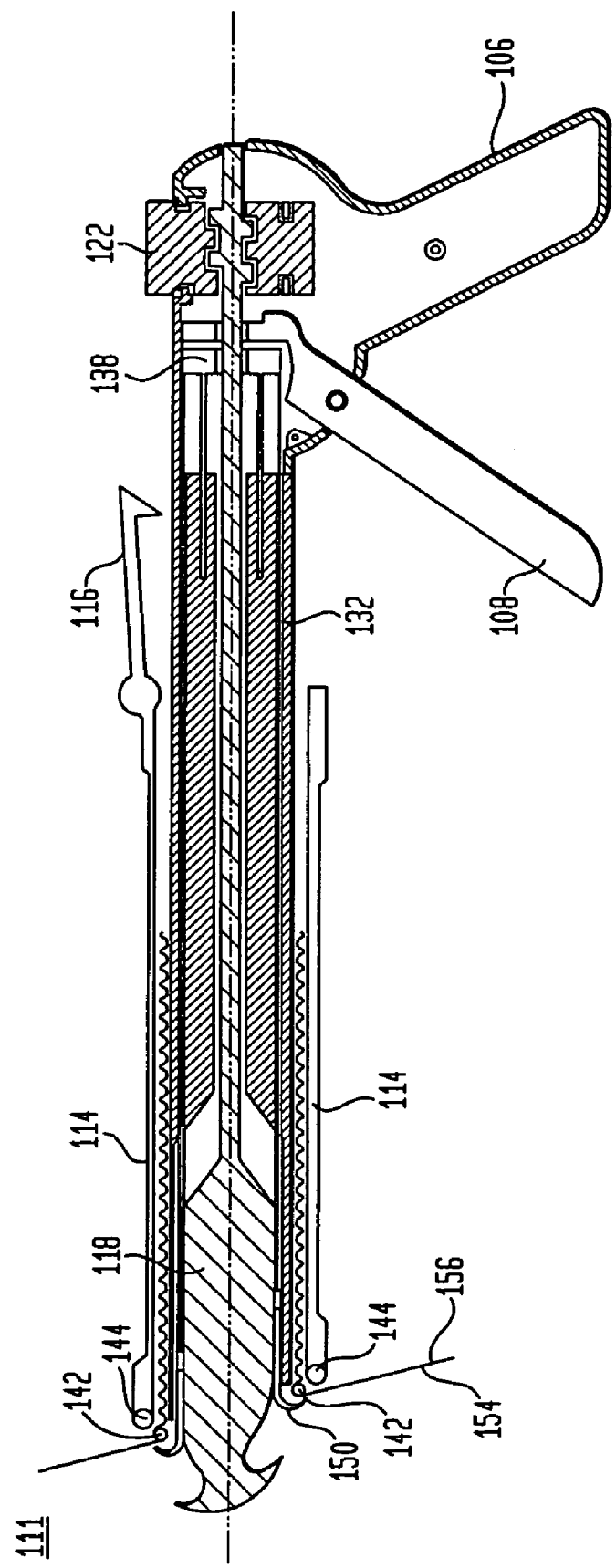

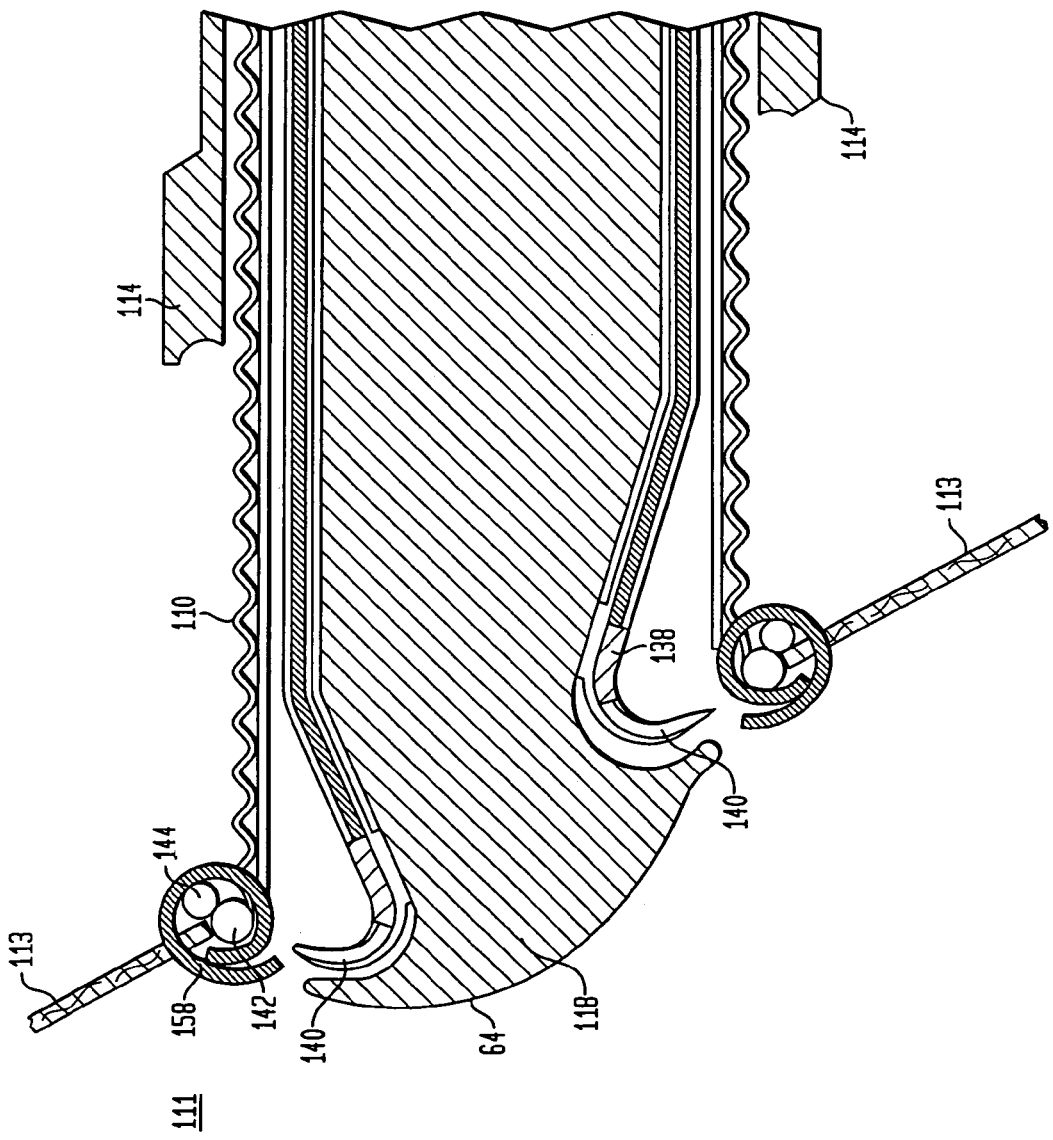

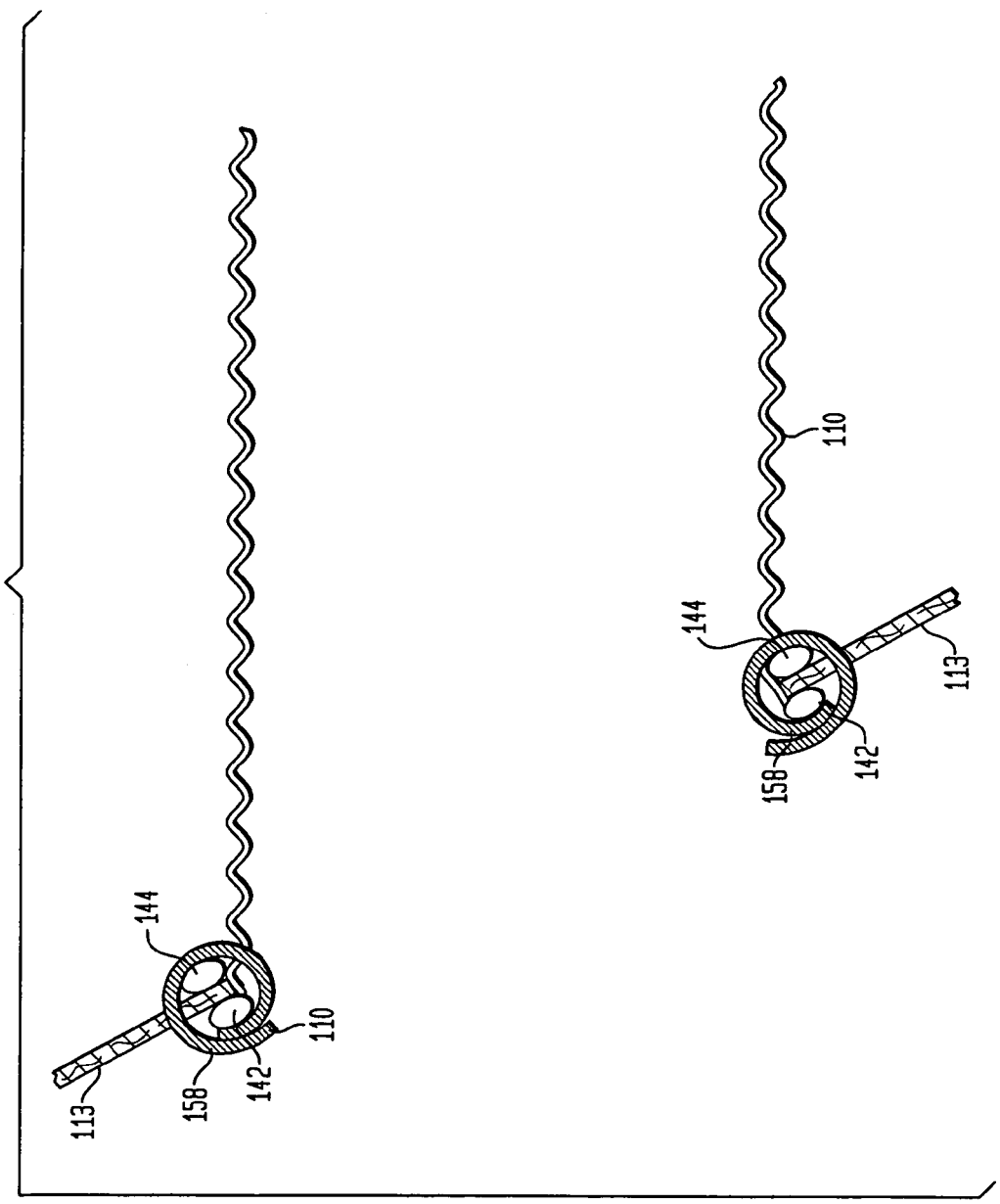

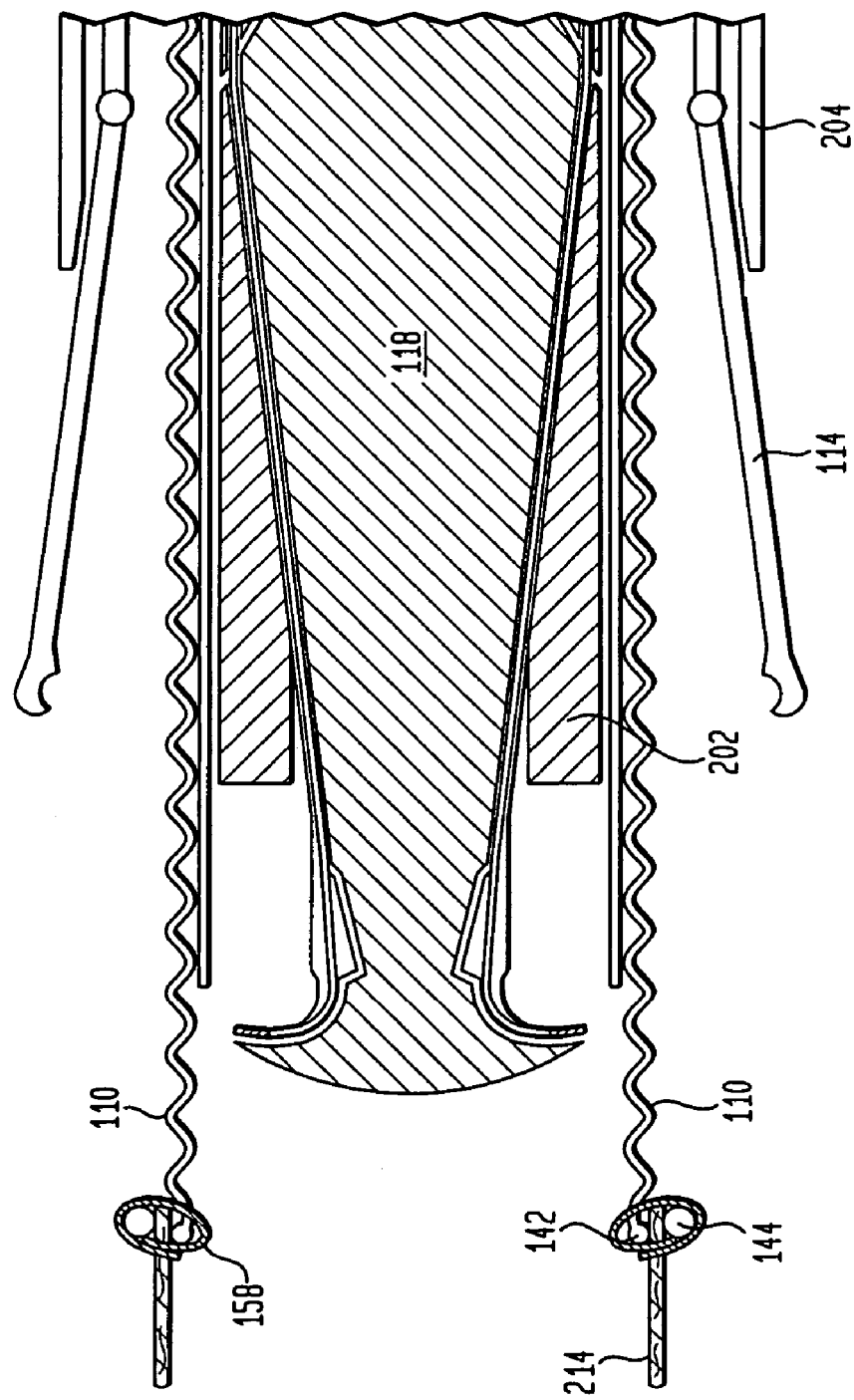

MULTIPLE STAPLING DEVICE FOR NARROW BLOOD VESSELS

CROSS REFERENCE TO RELATED APPLICATIONS

The present application relates to U.S. Provisional Patent Application Ser. No. 60/433,687 filed Dec. 16, 2002, the disclosure of which is hereby incorporated herein by reference.

BACKGROUND OF THE INVENTION

The present invention relates to a stapling device for use in the fixation of grafts to the walls of vessels in an end-to-side anastomosis or to the end of vessels in an end-to-end anastomosis.

It is known that grafts may be sutured to vessels manually by stitching. However, this method is tedious and time consuming, and is often inappropriate for specialized surgical procedures that require quick and accurate completion. Accordingly, various methods for enhancing the speed and quality of such anastomoses have been contemplated.

For example, it is known that a surgical stapler may join a graft to a vessel, such as a blood vessel, by injecting staples in a radial direction relative to the axis of the blood vessel. Typically, each of the staples may be positioned radially about a centerline of the stapler and may be discharged simultaneously. Such devices typically include anvils located outside of the blood vessel for forming the staples. Typical staples used in this type of stapler are C-shaped, similar to those used in a traditional office staplers.

Other known staplers include single shot anastomoses instruments with detachable loading units. Again, fasteners used in devices of this type are typically C-shaped. In addition, these fasteners of this type are typically clips that are not intended to pierce the vessels being anastomosed.

In the prior art devices, a prosthesis anastomosed to a vessel. The prosthesis typically has a consistent cross-sectional area. Thus, there is no reinforcement of the vessel or prosthesis. This can lead to tears or loosening of the anastomosis.

It would therefore be beneficial to bolster the prosthesis in the area to be stapled, to improve the purchase between the staple and the prosthesis, as well as for other reasons. It would also be advantageous to introduce a multiple stapling device for narrow blood vessels which utilizes ring-shaped staples. Finally, it would be beneficial to provide a multiple stapling device which overcomes other disadvantages and deficiencies of the prior art.

SUMMARY OF THE INVENTION

The shortcomings of the prior art have been addressed by the present invention, which in one preferred embodiment provides a multiple stapling device comprising a housing adapted for storing a plurality of straight wire segments therein, said housing having a plurality of exit areas for discharge of said straight wire segments therethrough; an actuating assembly adapted for discharging said plurality of straight wire segments through said plurality of exit areas; and, a prosthesis situated about said housing, said prosthesis having a bolster arranged at said exit areas; wherein said straight wire segments are formed into ring-shaped staples piercing said prosthesis and in communication with said bolster when discharged.

In another embodiment, the multiple stapling device for attaching a vascular prosthesis to a vessel comprises a body forming an outer housing having a proximal end and a distal end with a longitudinal axis extending therebetween, the outer housing having a hollow interior; an obdurator extending along the longitudinal axis of the outer housing, the obdurator partially filling the hollow interior within the outer housing; a housing filler situated between the obdurator and the outer housing, the housing filler including therein a plurality of shaped passages, the shaped passages extending substantially perpendicular to the longitudinal axis of the outer housing; staple guides extending from the passages of the housing filler at the distal end of the outer housing, the staple guides adapted to be positioned in communication with a portion of the obdurator; at least one stapler anvil situated about an exterior portion of the outer housing; a trigger extending from the body; and a plurality of staple drivers extending within the passages of the housing filler, the staple drivers operatively engaged with the trigger such that the staple drivers are displaced toward the distal end of the housing upon actuation of the trigger; wherein a vascular prosthesis may be mounted on the outer housing such that the prosthesis may be anastomosed to a vessel by inserting the distal end of the outer housing into the vessel and firing a plurality of wire segments through the passages of the housing filler and the staple guides by actuation of the trigger, wherein the wire segments exit the staple guides along an arcuate path and form a plurality of circular staples penetrating the prosthesis and the vessel to attach the prosthesis to the vessel.

Also disclosed is a synthetic prosthesis for anastomosis within the human body having a proximal end and a distal end, the prosthesis further comprising a bolster at the distal end. The bolster may be formed from the rolling of the prosthesis.

BRIEF DESCRIPTION OF THE DRAWINGS

The subject matter regarded as the invention is particularly pointed out and distinctly claimed in the concluding portion of the specification. The invention, however, both as to organization and method of operation, together with features, objects, and advantages thereof will be or become apparent to one with skill in the art upon reference to the following detailed description when read with the accompanying drawings. It is intended that nay additional organizations, methods of operation, features, objects or advantages ascertained by one skilled in the art to be included within this description, be within the scope of the present invention, and be protected by the accompanying claims.

In regard to the drawings.

FIG. 6A depicts a longitudinal sectional view of the stapling device of FIG. 1 viewed at the step of FIG. 6;

FIG. 8 depicts a longitudinal sectional view of the distal end of the stapling device of FIG. 1 showing a still further step of a preferred method of the present invention;

FIG. 9 depicts a completed anastomoses in accordance with a preferred method of the present invention;

FIG. 14 depicts a longitudinal sectional view of the distal end of the stapler of FIG. 10 in yet a further step of a preferred method of the present invention;

DETAILED DESCRIPTION

Figure 1:
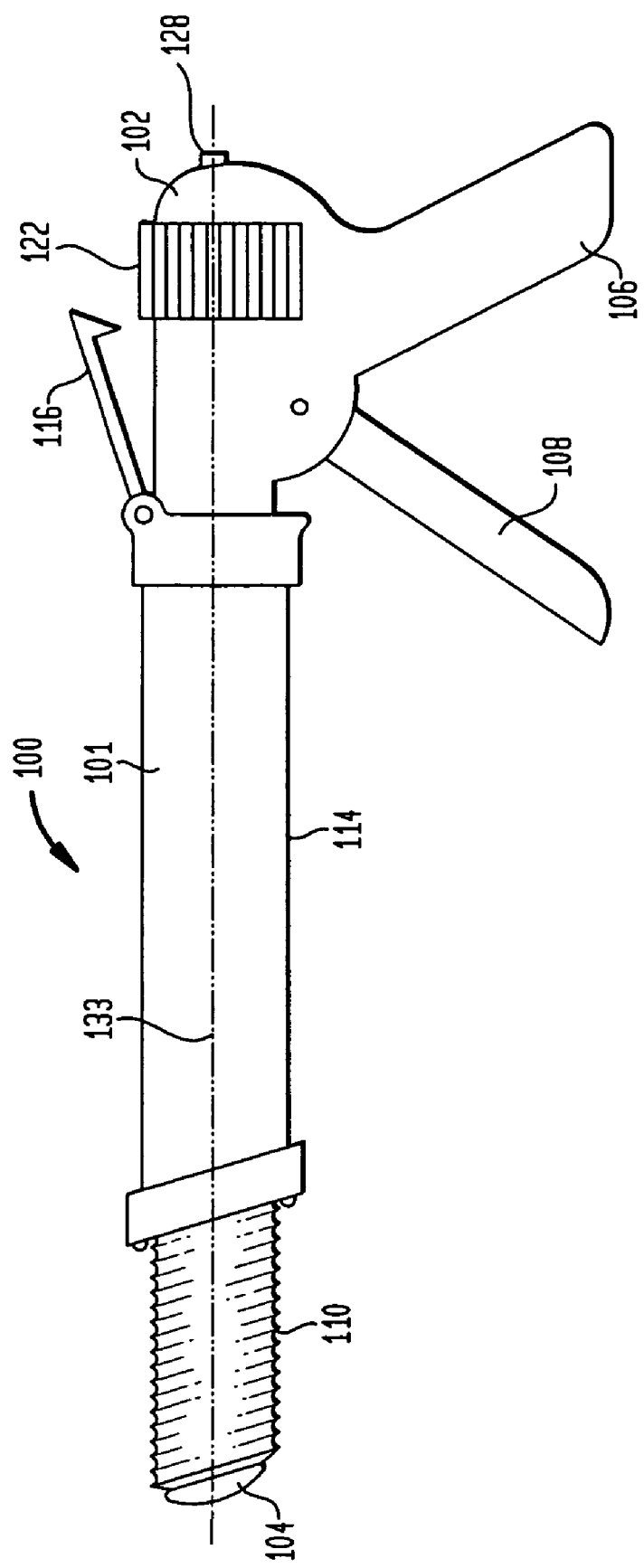
FIG. 1 is a side view of a multiple stapling device for narrow blood vessels in accordance with one embodiment of the present invention.

In the following is described the preferred embodiments of the multiple stapling device for narrow blood vessels. In describing the embodiments illustrated in the drawings, specific terminology will be used for the sake of clarity. However, the invention is not intended to be limited to the specific terms so selected, and it is to be understood that each specific term includes all technical equivalents that operate in a similar manner to accomplish a similar purpose.

Referring to the figures, FIG. 1 depicts a side view of a stapler 100 for use in end-to-side vascular anastomoses. The stapler shown in FIG. 1 comprises a housing 101 having a proximal end 102 and a distal end 104. The proximal end 102 includes a handle 106 for manipulation of the instrument during a surgical procedure. The proximal end 102 also includes a staple firing trigger 108 to facilitate engagement of the staples (not shown) in the end-to-side anastomoses.

The housing 101 extends from the proximal end 102 along a longitudinal centerline 133 toward its distal end 104. Mounted on or adjacent to the distal end 104 of the stapler 100 is vascular prosthesis 110. The stapler anvil 114 lies between the distal end 104 and the proximal end 102 of the stapler 100, making up the mid-section of the housing 101. The stapler anvil 114 is preferably approximately 6-8 mm. in diameter to facilitate anastomosis of arteries in the 6-8 mm. diameter range. An anvil closing lever 116 is attached to the stapler anvil 114 near the proximal end 102 of the stapler 100. An oburator dial may protrude from the housing 101 between the anvil closing lever 116 and the proximal end 102 of the stapler 100.

Figure 2:
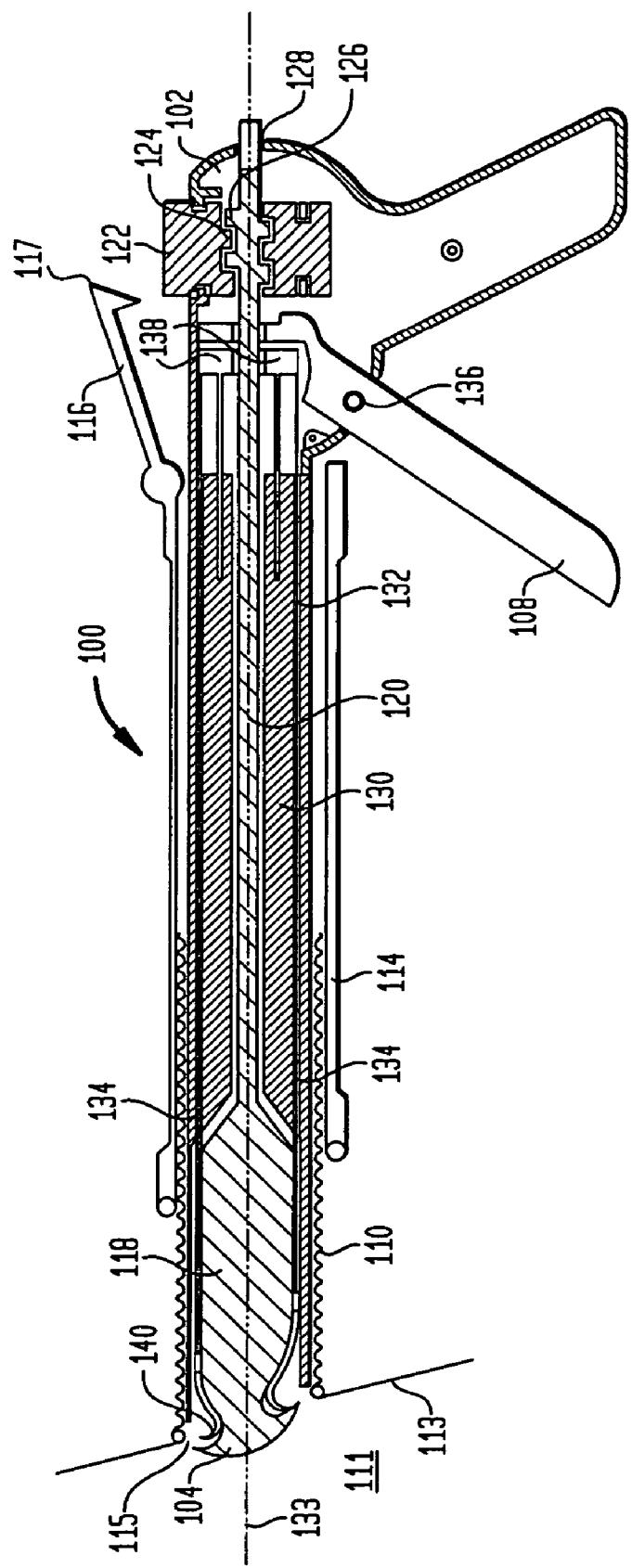
FIG. 2 is a longitudinal sectional view of the stapling device of FIG. 1 showing the internal components thereof.

FIG. 2 depicts a longitudinal section view of the stapler 100 shown in FIG. 1, such that the internal components may be viewed. As shown, within the distal end 104 of the stapler 100 may lie a stapler obdurator 118. The obdurator 118 may include a shaft 120 extending toward the proximal end 102 of the stapler 100 to its terminus just beyond the obdurator dial 122. Generally, the obdurator 118 is inflexible element.

The obdurator dial 122 communicates with the shaft 120 by way of engaged dial gears 124 and shaft gears 126 such that rotation of the obdurator dial 122 will advance or retract the stapler obdurator 118 from the distal end 104 of the stapler 100. It will be appreciated that the proximal end 102 of the stapler 100 includes a shaft aperture 128 which permits the shaft 120 to extend from within the proximal end 102 of the stapler 100 when the stapler obdurator 118 is in its retracted position toward the proximal end 102 of the stapler.

The shaft 120, particularly the portion extending from within the proximal end 102 of the stapler 100, may include etchings at measured intervals to assist the surgeon in determining when the stapler obdurator 118 has been fully advanced or fully retracted. If so provided, the surgeon will be assured that the staple guides 140 have been completely returned to within the recessed portion 148 of the obdurator 118 prior to withdrawal of the stapler 100, as will be discussed.

The stapler housing filler 130 surrounding the shaft 120 and the stapler obdurator 118 include a plurality of passages 132 extending longitudinally from the stapler obdurator 118 to the staple firing trigger 108. Each passage 132 contains straight wire segments 134 designed to be formed into circular staples (not shown).

A typical stapler 100 may contain any number of such passage 132. However, it is advantageous that they contain approximately eighteen (18) to twenty (20) passages 132 housing an equal number of straight wire segments 134. Each of the passages 132 is typically spaced with radial symmetry about the longitudinal center line 133 of the shaft 120. Each of the straight wire segments 134 is of a caliber and length sufficient for the intended anastomosis. The caliber is typically 0.20 mm. in diameter, while the length is typically sufficient to permit approximately 1 mm. of overlap when the circular staple (not shown) is formed. The length of the wire 134 and the stapler 100 should also be sized such that one stroke of the staple-firing trigger 108 will fully discharge the straight wire segments 134 from the passages 132, as will be described hereinafter.

The stapler anvil 114 surrounds the stapler housing filler 130 as shown in FIG. 2. The stapler anvil 114 may be retracted toward the proximal end 102 of the stapler 100 or advanced toward the distal end 104 of the stapler by manipulating the anvil closing lever 116. For example, opening the lever, such that the end portion 117 is farthest from the obdurator dial 122 may bring the stapler anvil 114 toward the proximal end 102 of the stapler 100, in a retracted position while closing the lever extends the anvil toward the distal end 104 of the stapler.

Drawing of the staple firing trigger 108 about pin 136 toward the handle 106 induces translation of staple drivers 138, which extend into passages 132 toward the distal end 104 of stapler 100. As will be discussed hereinafter, one full movement of the staple firing trigger 108 will cause the staple drivers 138 to engage the straight wire segments 134 and displace the straight wire segments into hooked staple guides 140 to form the circular staples (not shown) connecting the vessel wall 113 to the vascular prosthesis 110. Other firing mechanisms which do not resemble a trigger, but which provide a similar operation to control the staple drivers 138 and/or straight wire segments 134 are also contemplated. One example is a rotational dial similar to the obdurator dial 122. Such a rotational dial may be rotated a given number of turns to import the requisite translation of the staple drivers 138.

Figure 3:
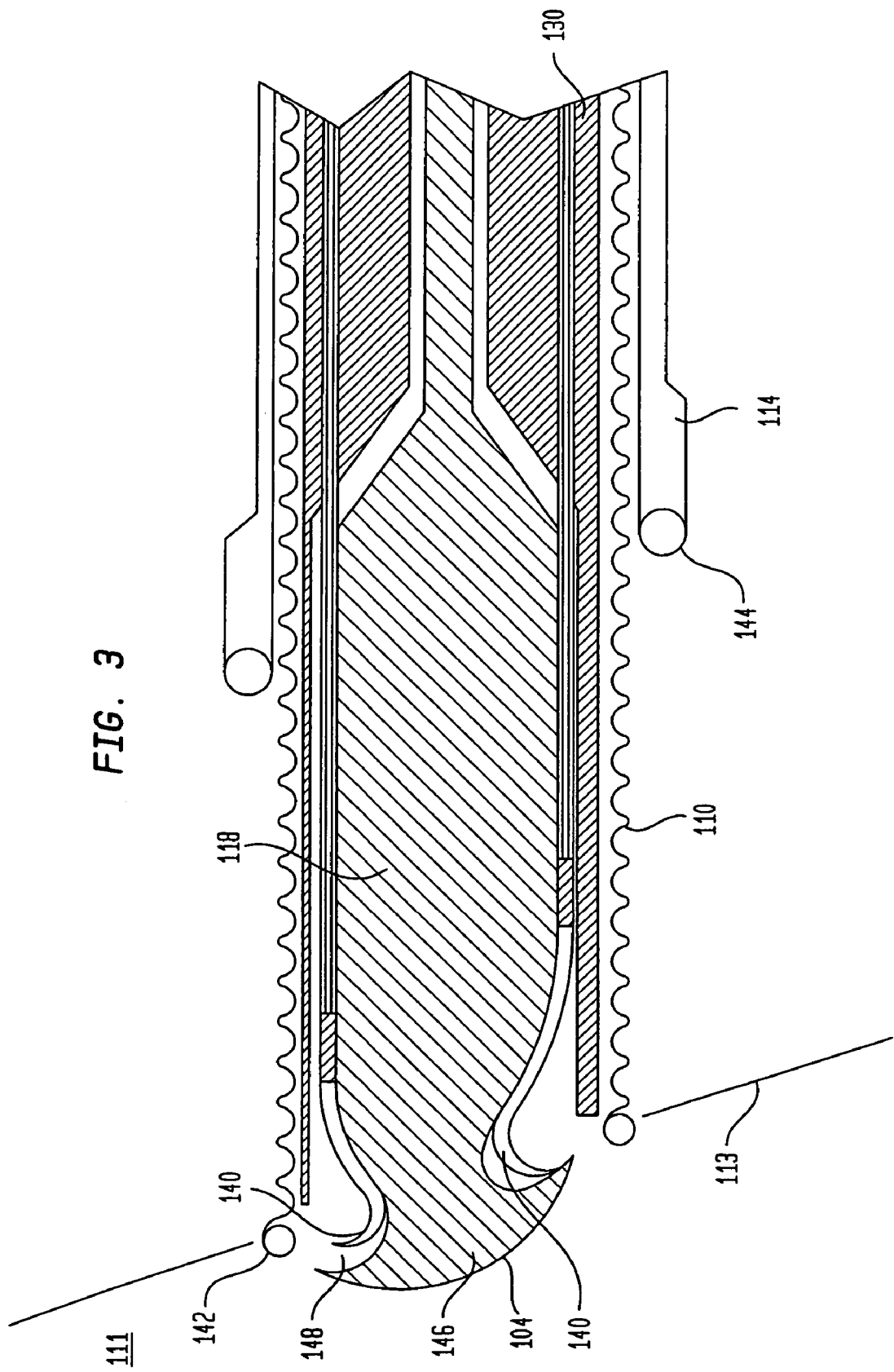
FIG. 3 is a longitudinal sectional view of the distal end of the stapling device of FIG. 1.

FIG. 3 depicts a magnified sectional view of the distal end 104 of the stapler 100 shown in FIGS. 1 and 2. As can clearly be seen, the vascular prosthesis 110 is arranged between the stapler anvil 114, which forms the outermost shell of the stapler 100, and stapler housing filler 130. Attached to the vascular prosthesis 110 at its distal end adjacent the distal end 104 of the stapler 100 is a prosthesis bolster 142.

The specialized vascular prosthesis 110 is typically manufactured from Dacron®, PTFE or other suitable material useful for such purposes. The prosthetic bolster 142 is generally formed integrally with the vascular prosthesis 110, and is typically made from Teflon® or Dacron®. Both Teflon® and Dacron® are registered trademarks of E.I. DuPont de Nemours and Company, 1007 Market Street, Wilmington, Del. 19898. The bolster 142 may also be a fiber material, such as polymer fiber, or a modified bovine pericardium strip. Again, it also can be made from any material which is suitable for surgery and which meets the objectives set forth herein.

The prosthetic bolster 142 may be formed simply by everting and rolling the vascular prosthesis 110 until such time that a bolster of sufficient size is formed. The bolster 142 may also be formed separately from the vascular prosthesis 110 and then attached using any biologically compatible means (physical, adhesive, etc.), including heated fusion or chemical bonding.

An anvil bolster 144 may also be provided. This bolster 144 is essentially a separate O-ring. The anvil bolster 144 is typically formed from Teflon® or Dacron®, and is typically a ring of material sized approximately equal to the diameter of the anvil 114. Typically, the anvil bolster 144 is of a greater diameter than the prosthesis bolster 142. The anvil bolster may also be a full ring with interrupted portions. Each of the interrupted portions may comprise larger diameter portions separated by smaller diameter portions. It will be appreciated that the larger diameter portions will typically be located at the anvils, so they may be included within the ring-shaped staples.

To facilitate healing following the surgical procedure the anvil bolster 144 may be impregnated with a haemostatic agent. In addition, the prosthesis bolster 142 may also be impregnated. However, the risk of the haemostatic agent leaching into the vessel from the prosthesis bolster 142 may render such impregnation too risky. Haemostatic agents are known in the art. As will be shown, the anvil bolster 144 may be placed into position for anastomosis by the anvil 114.

As clearly shown in FIG. 3, the stapler obdurator 118 includes a head 146 nearest the distal end 104 of the stapler 100. The stapler obdurator head 146 includes a recessed portion 148 within the cylindrical stapler obdurator 118 within which the hooked staple guides 140 may rest.

Figure 4:
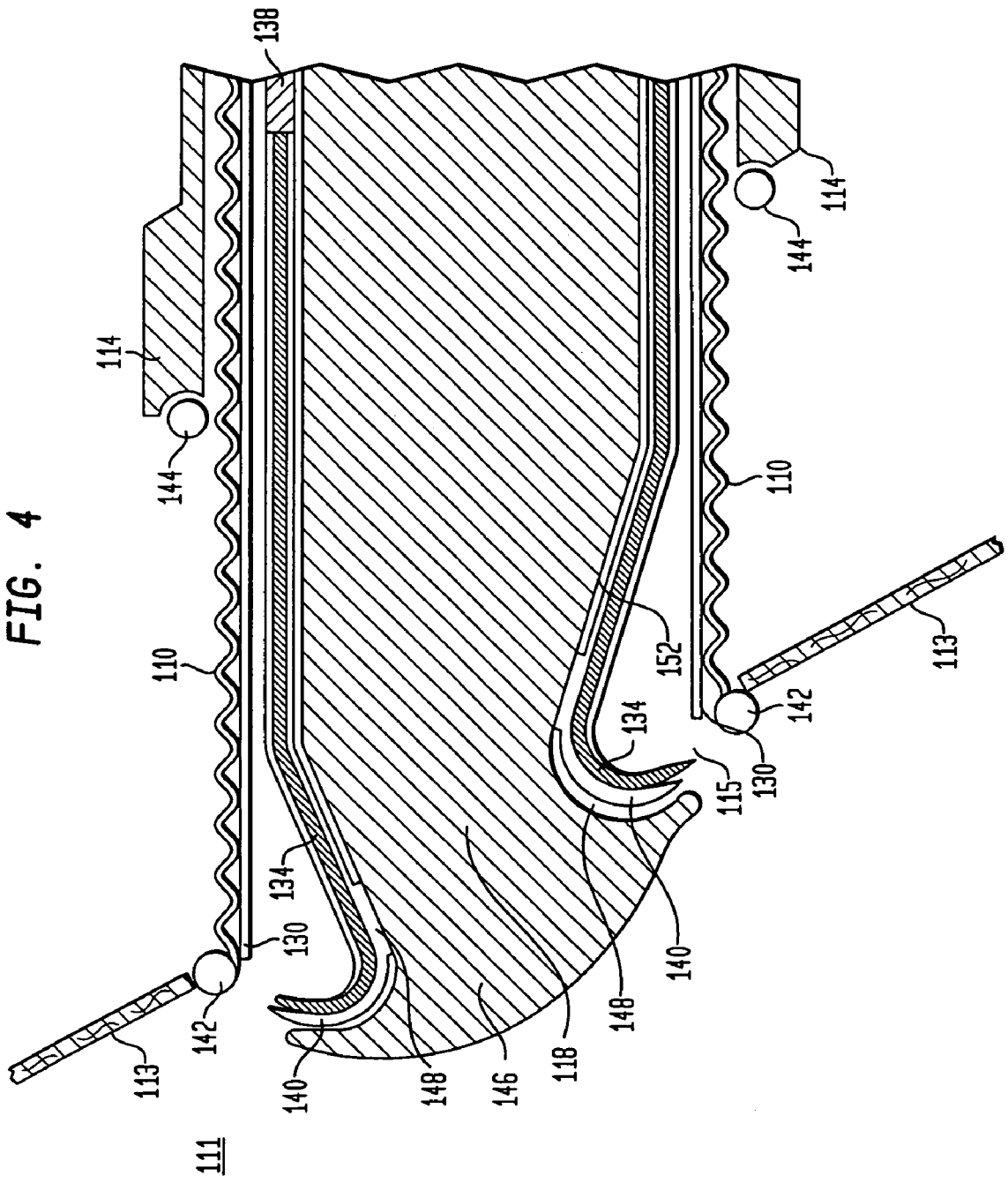
FIG. 4 is a longitudinal sectional view of the distal end of the stapling device of FIG. 1 showing a first step of a preferred method of the present invention.

Operation of the stapler 100 facilitates end-to-side anastomoses of a vascular prosthesis 110 to the wall 113 of a vessel 111. FIG. 4 depicts a magnified longitudinal section view of the distal end 104 of the stapler 100 positioned at the first step of this procedure. As shown, the distal end 104 of the stapler 100, including the vascular prosthesis 110 is typically inserted through a cavity 115 created in a vessel wall 113 and into the vessel 111 at the location where the vascular prosthesis 110 is intended to be permanently attached. It will be appreciated that the hooked staple guides 140 rest within the recessed portion 148 of the stapler obdurator 118 at this juncture of the procedure. Once inserted through the vessel cavity 115, the stapler obdurator head 146 may be advanced further into the vessel 111 by turning the obdurator dial 122 (FIG. 2) in a predetermined direction and for a predetermined number of turns. Other advancement mechanisms which provide accurate control and will not interfere with the other mechanisms of the stapler may also be used.

Figure 5:
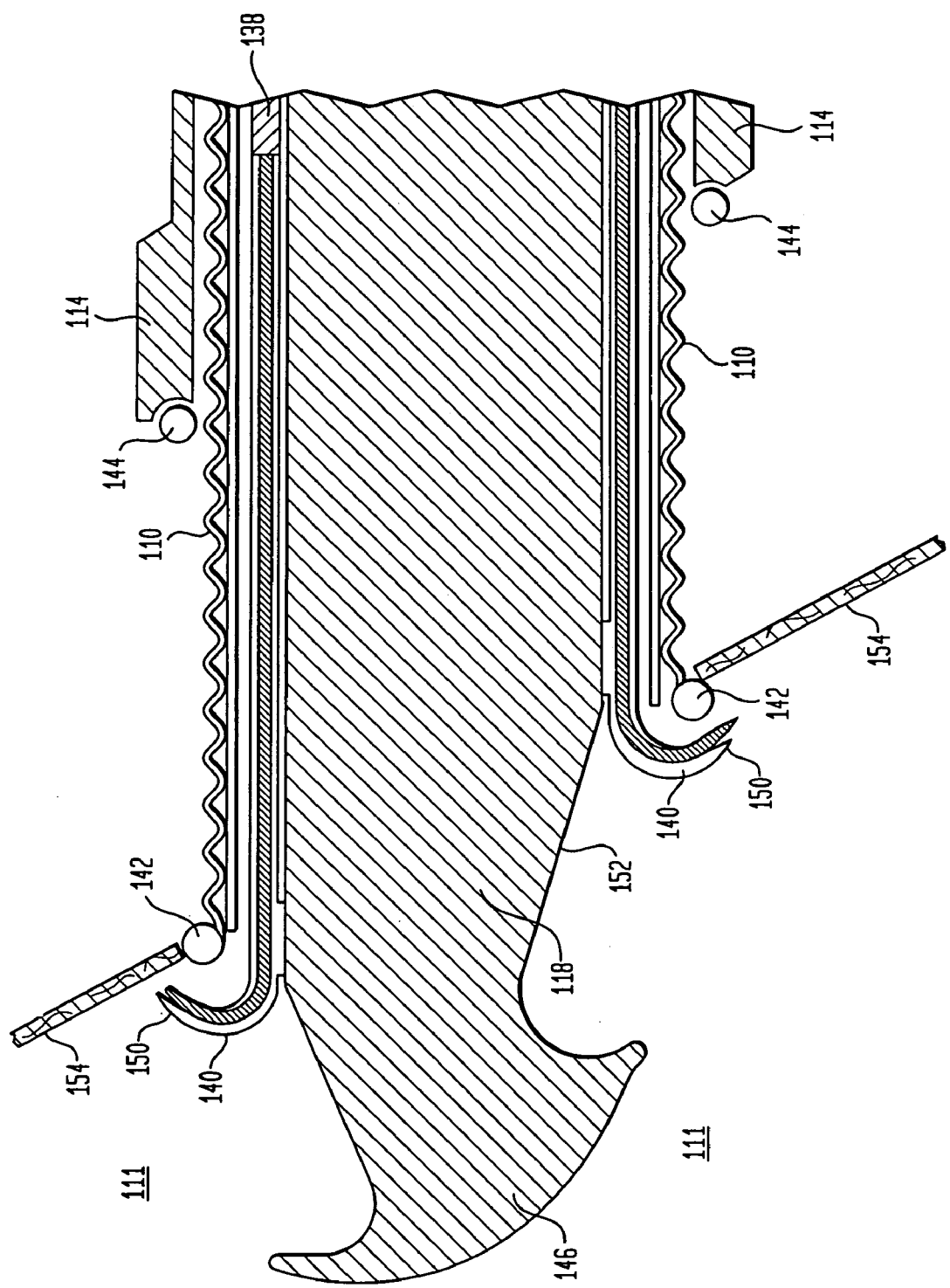
FIG. 5 depicts a longitudinal sectional view of the distal end of the stapling device of FIG. 1 showing a subsequent step of a preferred method of the present invention.

As shown in FIG. 5, advancement of the stapler obdurator 118 will cause the hooked staple guides 140 to expand outward due to the shape of the obdurator such that the end portion 150 will be beyond the limits of the prosthesis bolster 142. The staple guides 140 may advantageously be formed from a memory metal so they may readily return to their previous position upon retraction of the obdurator. Such expansion of the hooked staple guides 140 is achieved due to the strategically shaped ramped section 152 of the stapler obdurator 118 extending from the recessed portion 148 towards the proximal end 102 of the stapler 100. It will be appreciated that the length and angle of the ramped portions 152 should be calculated such that a given excursion of the obdurator 118 will cause the hooked staple guides 140 to expand the requisite amount. The obdurator excursion permitted may be a function of the vessel in which it inserted, if an opposing wall or other feature interferes.

Figure 16:
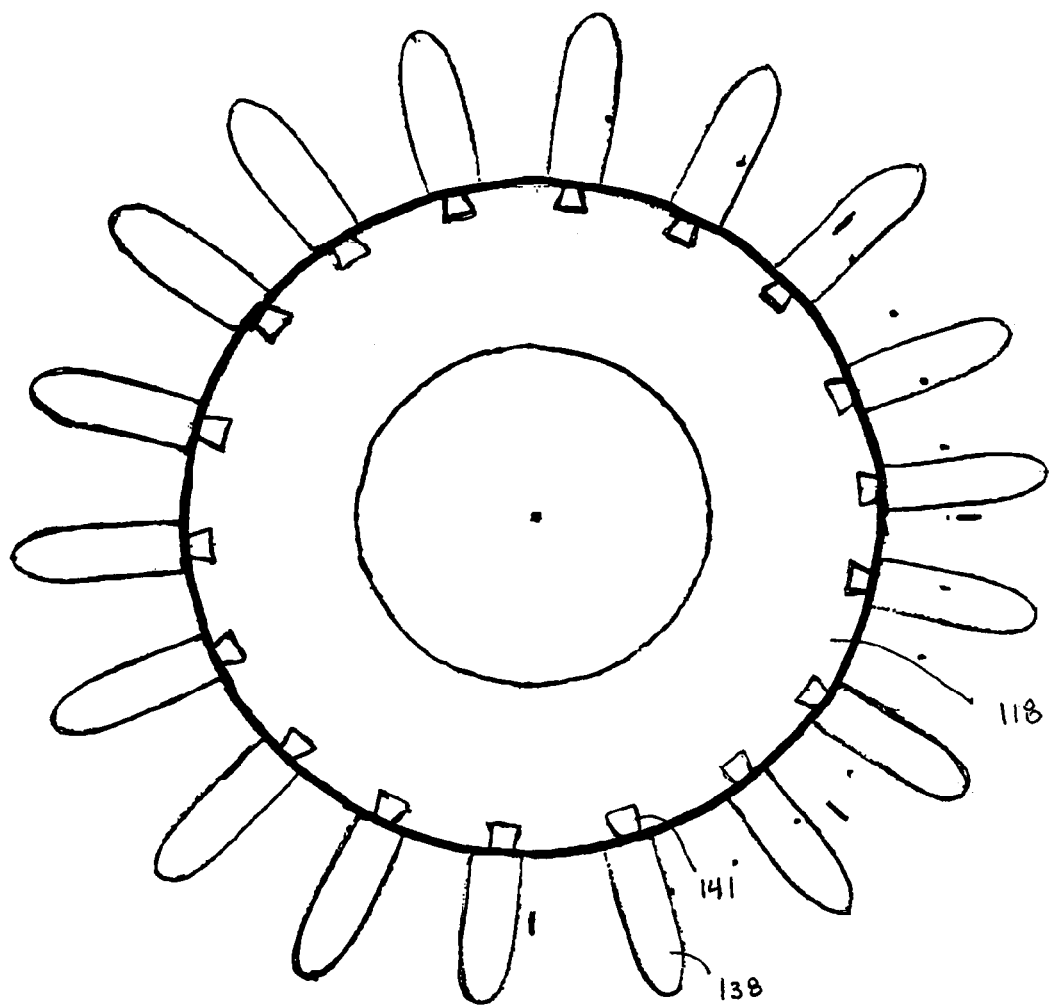

In addition, the staple guides 140 may be attached to tracks or slots 141 provided within obdurator 118. The tracks 141 not only guide the staple guides in a direction parallel to the longitudinal axis 133, but also inhibit the staple guides from shifting radially about the axis, such that they maintain an even radial spacing. FIG. 16 depicts a cross-sectional view of portions of the stapler 100 depicting an obdurator 118 with a plurality of tracks 141. Staple pushers 138 are shown both within the tracks 141, as well as beyond the tracks but within the staple channel (not shown).

Figure 5A:
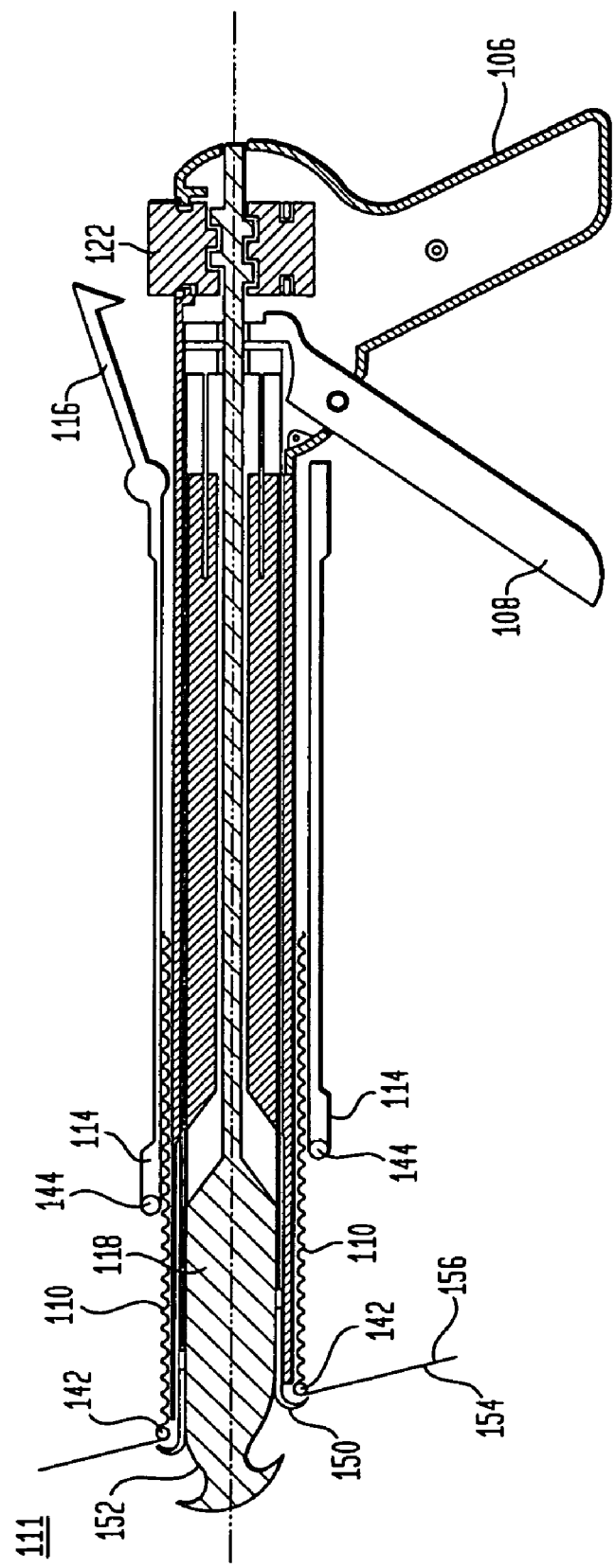
FIG. 5A depicts a longitudinal sectional view of stapling device of FIG. 1 viewed at the step of FIG. 5.
Figure 6:
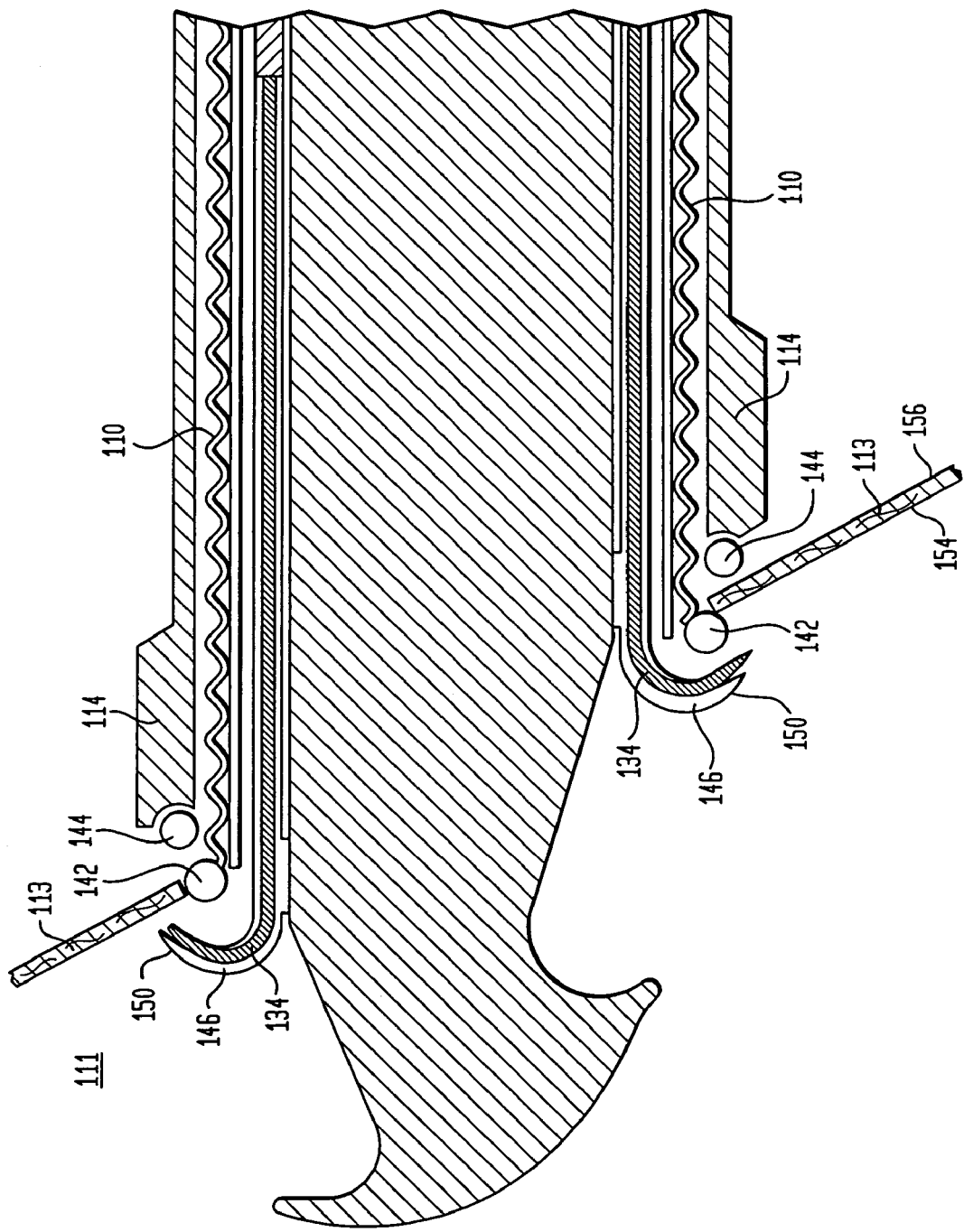
FIG. 6 depicts a longitudinal sectional view of the distal end of the stapling device of FIG. 1 showing still another step of a preferred method of the present invention.

FIGS. 5 and 5a depict the stapler obdurator 118 in its fully advanced position with the hooked staple guides 140 fully extended. Once in this position, the end portion 150 of the hook staple guides 140 may be placed in proximity with the intimal surface 154 of the vessel 111. Once thus positioned, the anvil closing lever 116 (FIG. 5a) may be closed such that the stapler anvil 114 will be advanced towards the distal end 104 of the stapler 100. In its fully extended position, stapler anvil 114 will cause anvil bolster 144 to come into proximity to, or communication with, the adventitial surface 156 of the vessel wall 113. This position is shown in FIGS. 6 and 6a, where the anvil bolster 144 and the prosthesis bolster 142 are generally opposed on opposite sides of the wall 113 of the vessel 111 and are trapped between the extended guides 150 and the stapler anvil 114 which hold them in position for stapling.

Figure 7:
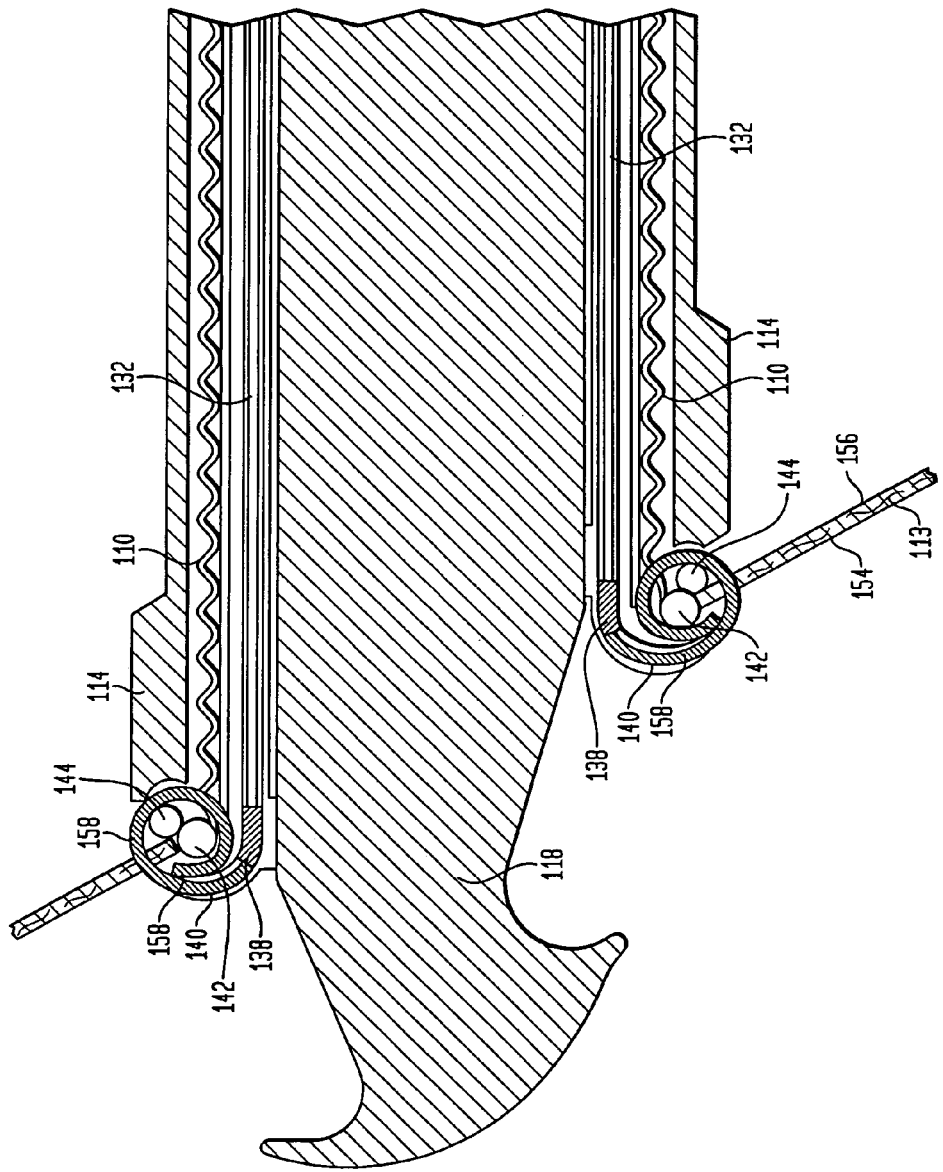
FIG. 7 depicts a longitudinal sectional view of the distal end of the stapling device of FIG. 1 showing a further step of a preferred method of the present invention.
Figure 7A:
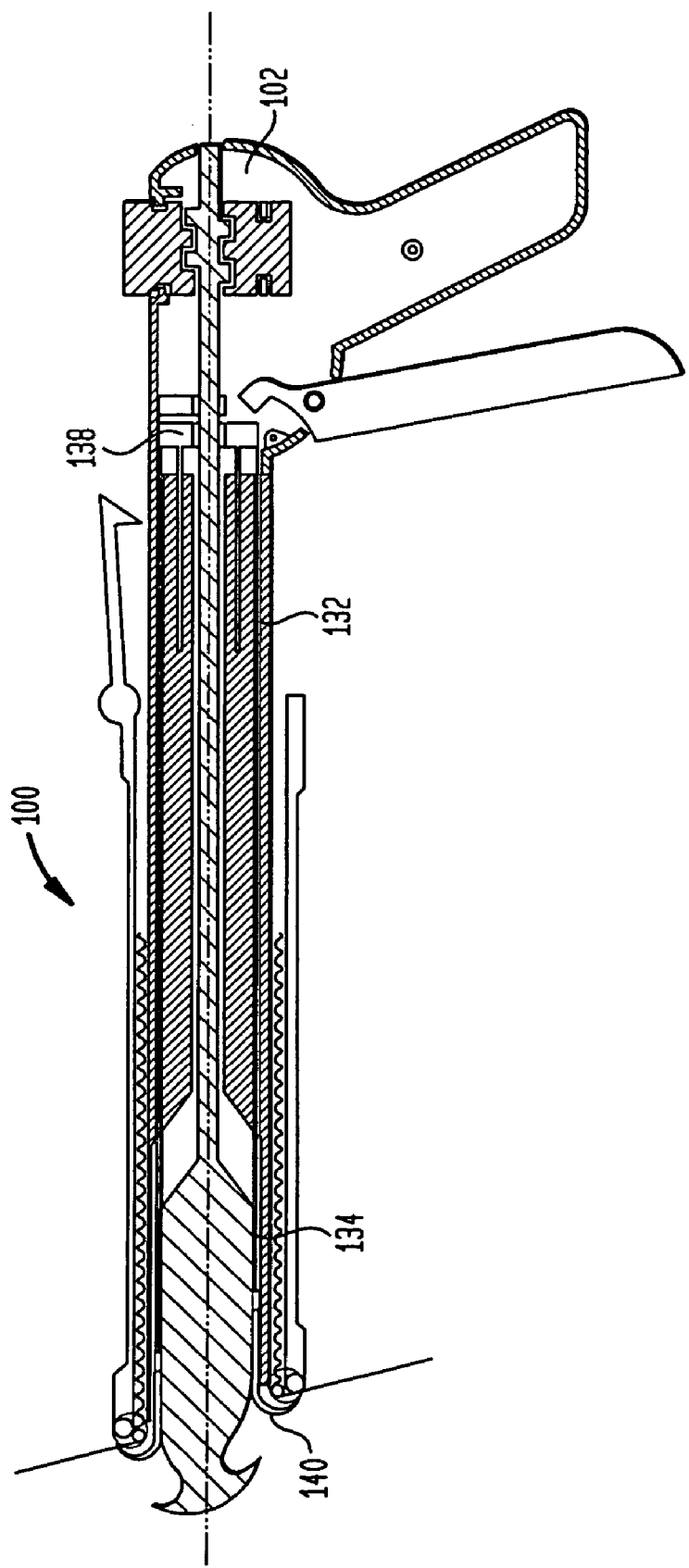
FIG. 7A depicts a longitudinal sectional view of the stapling device of FIG. 1 viewed at the step of FIG. 7.

At this juncture, the vascular prosthesis 110 is in a position for anastomoses to the vessel wall 113. This step is shown in FIGS. 7 and 7a, where the staple firing trigger 108 is squeezed toward the proximal end 102 of the stapler 100 to press staple drivers 138 into passages 132 and against straight wire segments 134. Such extension causes straight wire segments (not shown) to be displaced so as to slide within the passage 132 through the hooked staple guides 140. The hooked staple guides 140 cause the straight wire segments 134 to begin forming a circular shape where they become circular staples 158.

Upon exiting the hooked staple guides 140, the circular staples penetrate the intimal surface 154 of the vessel wall 113 and extend out of the adventitial surface 156 towards the vascular prosthesis 110. The staple will then pierce the vascular prosthesis 110 and continue to circle around into a substantially closed position inclusive of both the anvil bolster 144 and the prosthesis bolster 142. It is also possible, however, for the circular staple 158 to penetrate and extend through either or both the prosthesis bolster 142 or the anvil bolster 144. One object of the bolsters 142, 144 is to fill the annular space within the staple 158 not taken up by the vessel wall 113 or the prosthesis 110 to allow for rigid retention which does not apply such pressure as to completely end blood flow to that region of the vessel wall. Use of both bolsters is optional. In some embodiments, a single bolster may suffice. Either of the two may be eliminated.

Once the staples 158 have been fired as discussed, the anastomoses is substantially completed. The anvil bolster 144 previously attached to the stapler anvil 114 by a suitable biologic adhesive such as silicon, if any, will readily separate from the stapler anvil. The stapler anvil 114 may then be retracted by reverse operation of the anvil closing lever 116. The stapler obdurator 118 may also be retracted. This is accomplished by rotating the obdurator dial 122 in a direction opposite to the direction used for extension of the obdurator 118. Etchings on the shaft 120 may assist in the procedure, as previously discussed. FIG. 8 depicts this substantially complete anastomosis where the distal end 104 of the stapler 100 is ready to be removed from the vessel 111. A fully complete anastomosis is depicted in FIG. 9.

Figure 10:
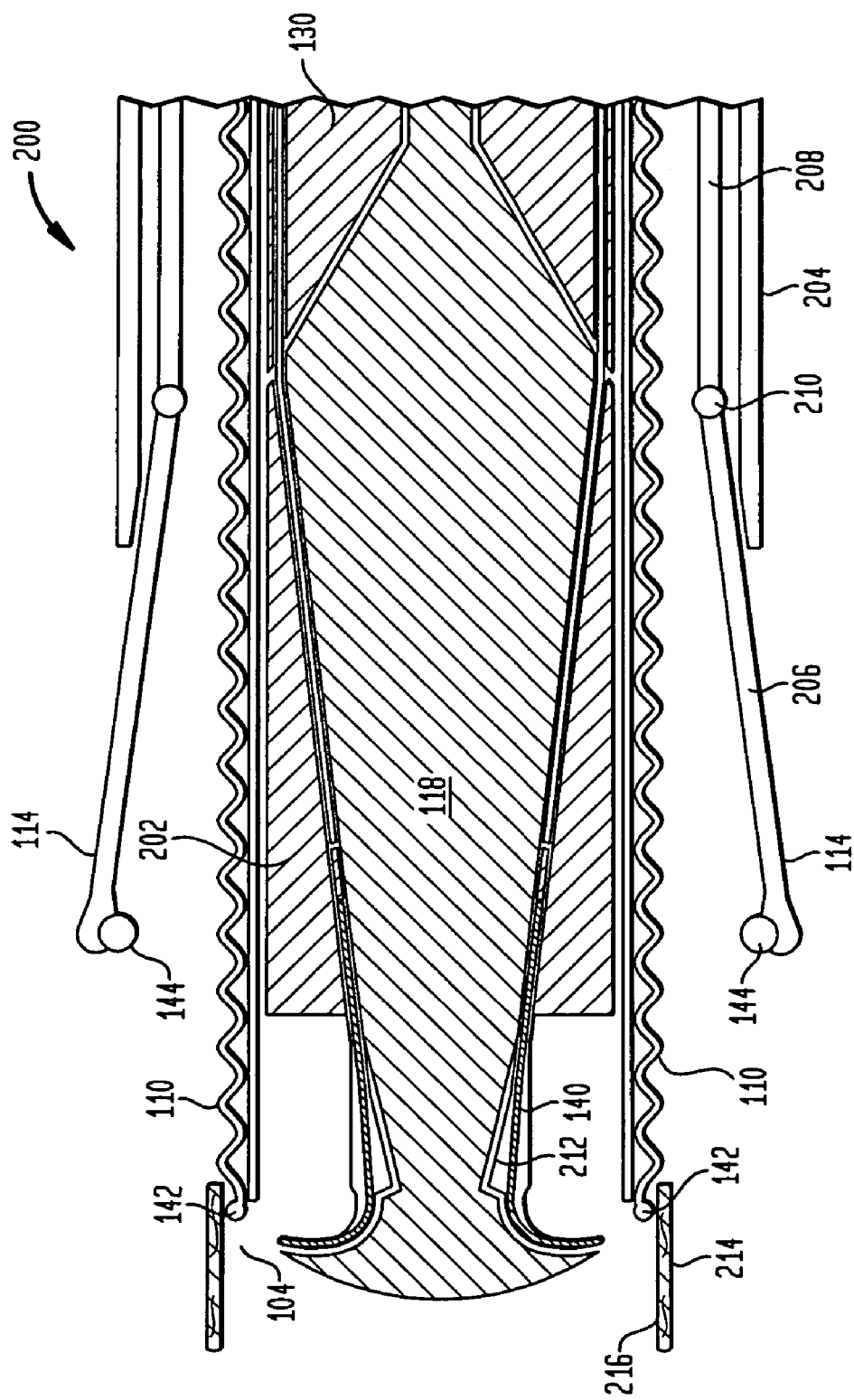
FIG. 10 depicts a longitudinal sectional view of the distal end of a multiple stapling device for narrow blood vessels in accordance with a second embodiment of the present invention in an initial step of a preferred method of the present invention.

FIG. 10 depicts a longitudinal section view of a stapler 200 in accordance with a second embodiment of the present invention. The stapler 200 in this embodiment is utilized to anastomose vessels in an end-to-end relationship. Where like elements in the following figures operate in the same manner as like elements in the preceding figures, common identification numerals have been utilized.

As shown in FIG. 10, stapler 200 comprises a stapler obdurator 118 at the stapler's distal end 104 with a shaft 120 extending toward the stapler's proximal end (not shown). As in the previous embodiment, a portion of the stapler obdurator 118 and the shaft 120 is in communication with the stapler housing filler 130 substantially filling the annular space within the stapler housing 101. Beyond the limits of the stapler housing 101 is a vascular prosthesis 110 complete with prosthesis bolster 142 at the distal end 104 of the stapler 200. As in the previous embodiment, a stapler anvil 114 extends over the vascular prosthesis 110. However, the stapler anvil 114 in this embodiment does not form the outermost shell of the stapler 200. In this embodiment, an anvil closure sheath 204 does.

Stapler guide 140 is located between the stapler obdurator 118 and stapler obdurator filler 202. The stapler guide 140 is aligned with passages 132 through the housing filler 130.

It will be appreciated that the stapler anvil 114 of this embodiment is hinged in a bi—or tripartide configuration. Other configurations are also possible. The stapler anvil 114 shown in FIG. 10 is a bipartite configuration having a first section 206 and a second section 208 connected by a hinge 210.

Operation of the stapler 200 of the second embodiment is substantially similar to the operation of the stapler 100 in the first embodiment. However, there are several differences. One of these differences is that the stapler obdurator 118 contains a ramped section 212 which is less steep than the ramp section 152 of the stapler obdurator of the previous embodiment. Thus, when the stapler obdurator 118 is extended beyond the distal end of the stapler 200, the hooked staple guides 140 flare out to a much lesser degree than the staple guides of the previous embodiment. Another difference is the bi—or tripartide configuration of the stapler anvil, as previously discussed.

The stapler 200 complete with vascular prosthesis 110 with bolster 142 may be inserted into a blood vessel 214 such that the bolster is adjacent the intimal surface 216 of the blood vessel 214. Once inserted therein, the stapler obdurator 118 may be extended beyond the distal end 104 of the stapler 200 by use of the obdurator dial (not shown), as in the previous embodiment.

Figure 11:
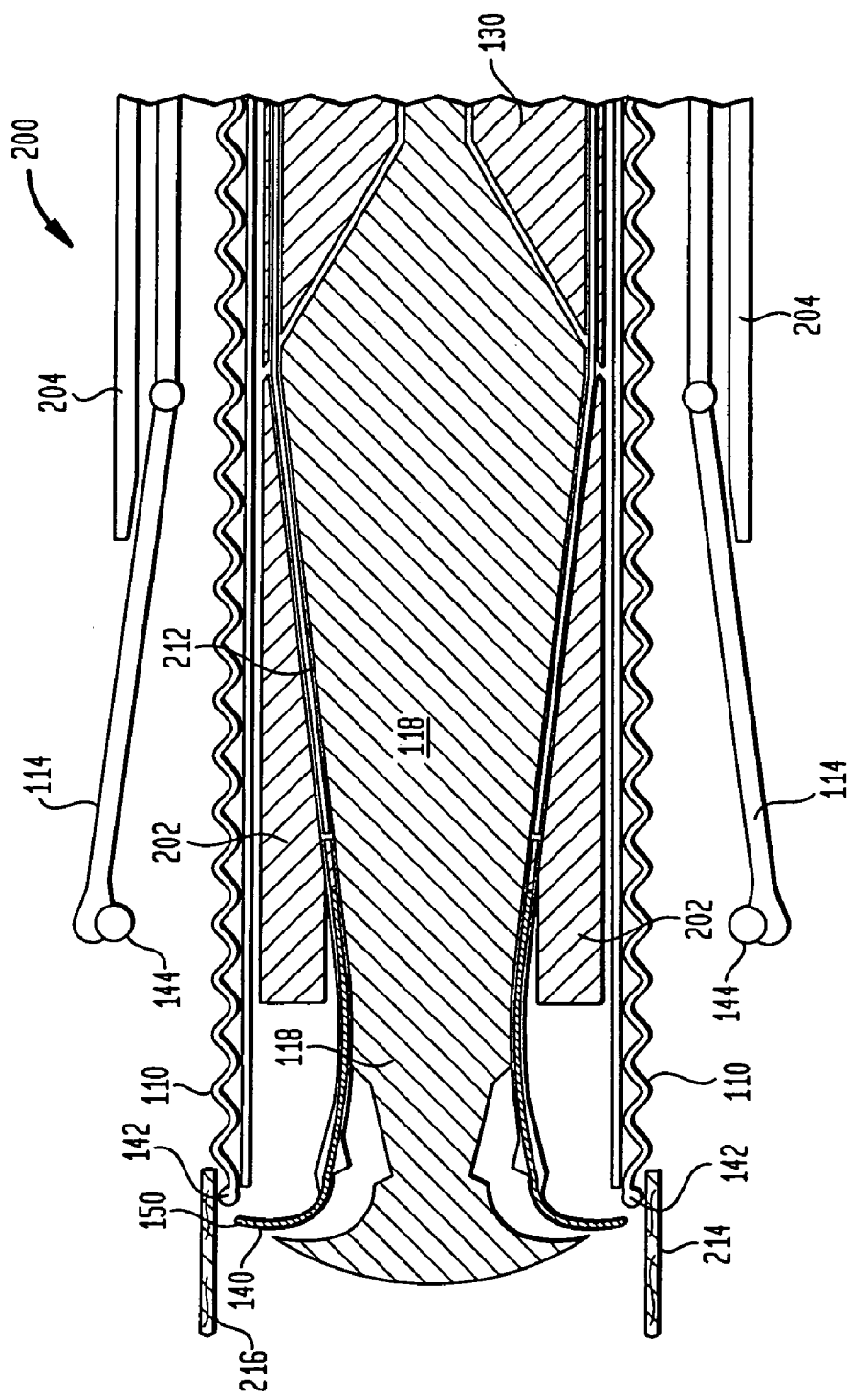
FIG. 11 depicts a longitudinal sectional view of the distal end of the stapler of FIG. 10 in a subsequent step of a preferred method of the present invention.

FIG. 11 depicts a stapler obdurator 118 in this extended position. It will be appreciated that because the ramp section 212 of the stapler obdurator 118 of the present embodiment is less steep than the ramp section 152 of the stapler obdurator 118 of the previous embodiment, the hooked staple guides 140 only flare out a minimal amount such that the hinged portion 150 is in close proximity or in communication with intimal surface 216 of blood vessel 214. A stapler in this device is depicted by FIG. 11.

Figure 12:
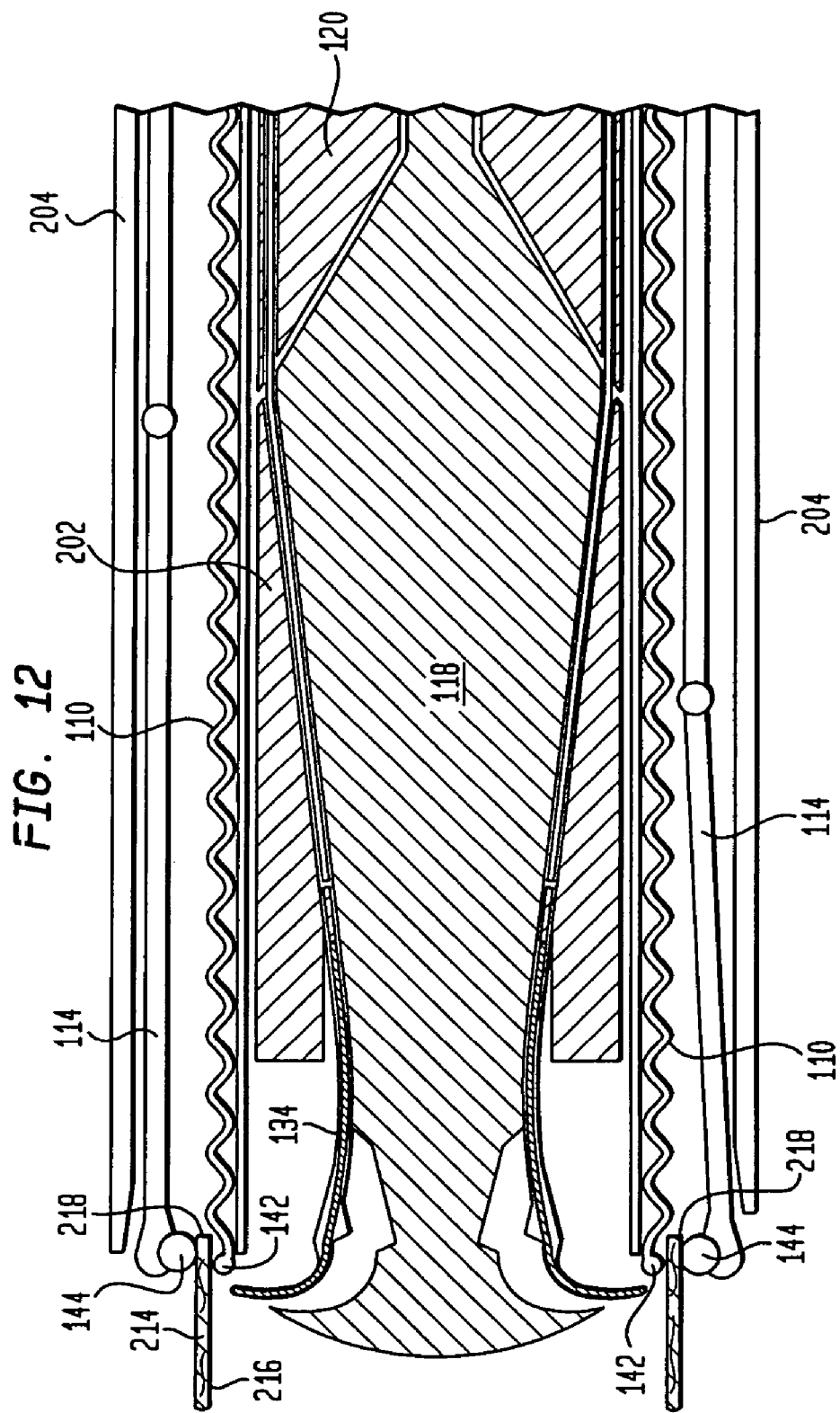
FIG. 12 depicts a longitudinal sectional view of the distal end of the stapler of FIG. 10 in another step of a preferred method of the present invention.

As shown in FIG. 12, the anvil closure sheath 204 and the stapler anvil 114 may then be extended out toward the distal end 104 of the stapler 200 such that the stapler anvil 114 and attached anvil bolster 144 buttress vascular prosthesis 142 to the intimal surface 216 of blood vessel 214. It will be appreciated that this buttressing occurs at the end 218 of blood vessel 214. As the anvil closure sheath 204 is advanced, it closes the staple anvil 114 sections which then encircle the prosthesis 110 with the bolsters 144, 142 opposed on opposite sides of the vessel wall 214. Advancement of the anvil closure sheath 204 may be conducted by simply sliding the sheath forward manually, or by use of the anvil closing level 116 in conjunction with movement of the stapler anvil 114. A separate anvil closure sheath lever (not shown) may also be provided. Other mechanisms which do not interfere with other aspects of the stapler 100 may also be provided.

Figure 13:
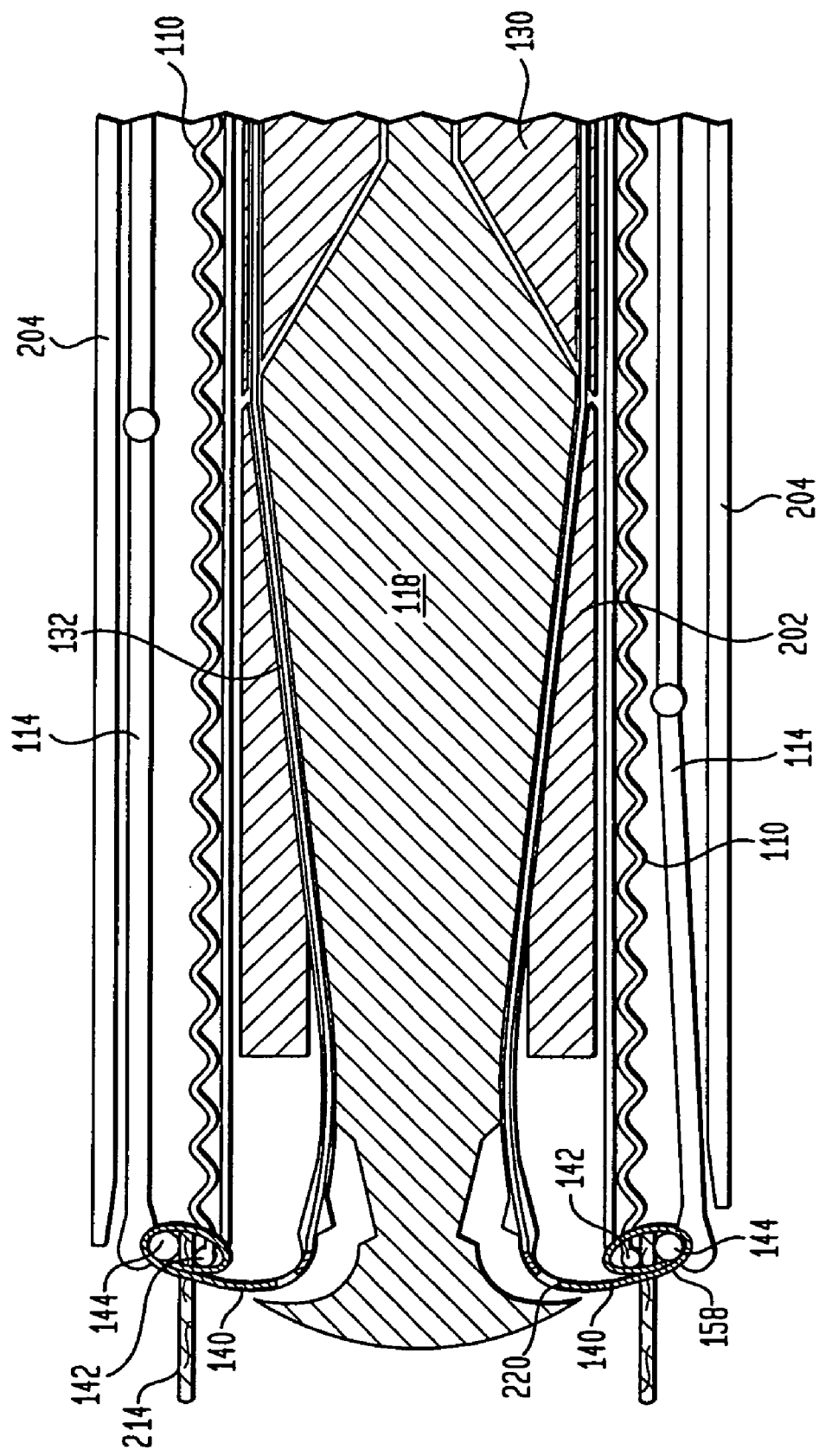
FIG. 13 depicts a longitudinal sectional view of the distal end of the stapler of FIG. 10 in a still further step of a preferred method of the present invention.

Once the stapler 200 is manipulated into the position shown in FIG. 12, the trigger (not shown) or other suitable mechanism may be pulled to fire staples 158, as shown in FIG. 13. As in the previous embodiment, straight wire segments 134 (FIG. 12) are displaced through passages 132 extending along the longitudinal axis of the stapler 200 and out through the staple guides 140. Once through the staple guides, the straight wire segments 134 penetrate the blood vessel 214 and curve either around or through the bolster 142 and/or anvil bolster 144 where they continue to curve toward the vascular prosthesis 110. The staple 158 then penetrates the vascular prosthesis 110 and continues around until there is approximately 1 mm. of overlap at the end portion 220 of the staple.

As with the previous embodiment, the annular space within the staple is filled by the anvil bolster 144 and/or the prosthesis bolster 142.

The stapler obdurator 118 may then be withdrawn along with the remainder of the stapler 200 to reveal an end-to-end anastomosis as shown in FIG. 14.

Figure 15A:
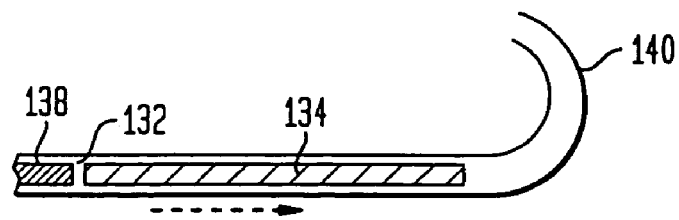
FIGS. 15A through 15D depict a staple being formed in accordance with preferred methods of the present invention; and, FIG. 16 depicts a cross-sectional view of portions of the stapler showing the arrangement of a plurality of staple drivers about an obdurator.
Figure 15B:
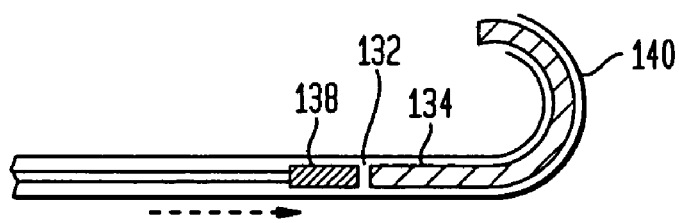
Figure 15C:
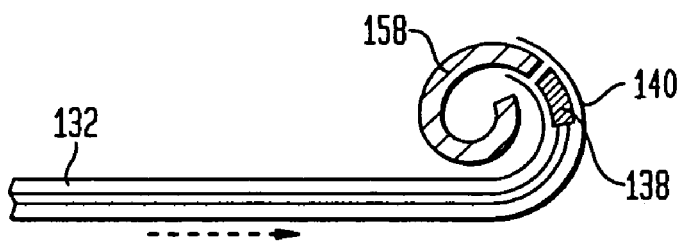
Figure 15D:
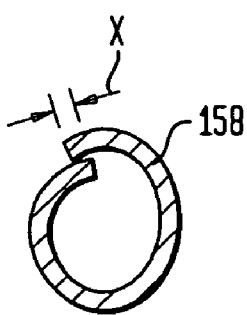

FIG. 15a depicts a straight wire segment 134 within the passage 132 of the stapler 100. As is shown, the straight wire segment 134 may be pushed by the staple driver 138 through the passage 132 and around the hooked staple guide 140. FIG. 15b depicts the straight wire segment 134 in a position farther advanced along the channel 132. FIG. 15c depicts a staple 158 formed from the straight wire segment 134 as it departs from the channel 132. It will be noted that the staple driver 138 continues to push the straight wire segment 134 through the staple guide 140. FIG. 15d depicts a completely formed staple 158 in accordance with preferred embodiments of the present invention. It will be appreciated that the staple 158 as shown overlaps a distance "x." This distance may be altered depending on the length of the straight wire segment 134 and the curvature of the hooked staple guide 140. Staples 158 with greater overlaps, or which loop around several times, are typically stronger than the staple 158 shown in FIG. 15d.

Among others, there are several advantages to the stapling device of the present invention over the prior art. First, because bolsters 142, 144 are provided, minimal impressions are made to the synthetic prosthesis 110 or the vessel 111 being attached. Also, use of the bolsters 142, 144 permits impregnation with haemostatic agents to promote healing of the anastomosis. The bolsters also fill the annular space within the staple 158 to prevent migration and strengthen the anastomosis. Other benefits have also been realized.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A multiple stapling device for attaching a vascular prosthesis to a vessel comprising:
   a body forming an outer housing having a proximal end and a distal end with a longitudinal axis extending therebetween, said outer housing having a hollow interior;
   an obdurator extending along the longitudinal axis of said outer housing, said obdurator partially filling said hollow interior within said outer housing;
   a housing filler situated between said obdurator and said outer housing, said housing filler including therein a plurality of passages;
   staple guides extending from said passages of said housing filler at said distal end of said outer housing, said staple guides adapted to be positioned in communication with a portion of said obdurator;
   at least one stapler anvil situated about an exterior portion of said outer housing;
   a trigger extending from said body; and
   a plurality of staple drivers extending within said passages of said housing filler, said staple drivers operatively engaged with said trigger such that said staple drivers are displaced toward said distal end of said housing upon actuation of said trigger;
   wherein a vascular prosthesis may be mounted on said outer housing such that said prosthesis may be anastomosed to a vessel by inserting the distal end of said outer housing into the vessel and firing a plurality of wire segments through said passages of said housing filler and said staple guides by actuation of said trigger, wherein the wire segments exit said staple guides along an arcuate path and form a plurality of circular staples penetrating the prosthesis and the vessel to attach the prosthesis to the vessel.

2. The multiple stapling device of claim 1, further comprising an anvil bolster in communication with said stapler anvil, said bolster becoming incorporated with the prosthesis, the vessel, and the staples upon anastomosis.

3. The multiple stapling device of claim 1, wherein said prosthesis includes a prosthesis bolster, said prosthesis bolster being incorporated with the prosthesis, the vessel, and the staples upon anastomosis.

4. The multiple stapling device of claim 1, further comprising an anvil bolster in communication with said stapler anvil and wherein said prosthesis includes a prosthesis bolster near said distal end of said outer housing, said anvil bolster and said prosthesis bolster being incorporated with the prosthesis, the vessel and the staples upon anastomosis.

5. The multiple stapling device of claim 4, wherein the staples are adapted to form rings and said bolsters substantially fill the annular space created by said rings.

6. The multiple stapling device of claim 4, wherein said plurality of passages are situated with radial symmetry about said longitudinal axis.

7. The multiple stapling device of claim 4, further comprising an obdurator advancement mechanism, said obdurator advancement mechanism comprising a geared shaft extending from said obdurator to said proximal end of said housing and a geared dial in communication with said geared shaft and said exterior of said outer housing, wherein rotation of said geared dial moves said obdurator in a predetermined direction.

8. The multiple stapling device of claim 7, wherein said shaft is adapted to extend through the body.

9. The multiple stapling device of claim 8, wherein said shaft includes demarcations to indicate the general location of the obdurator.

10. The multiple stapling device of claim 4, wherein said prosthesis bolster is formed from said prosthesis.

11. The multiple stapling device of claim 4, wherein said prosthesis bolster is attached to said prosthesis.

12. The multiple stapling device of claim 4, wherein at least one of said prosthesis bolster and said anvil bolster are impregnated with a haemostatic agent.

13. The multiple stapling device of claim 4, further comprising an anvil closure lever in communication with said body, said anvil closure lever adapted to advance said at least one anvil toward said distal end of said outer housing when rotated in a first direction and away from said distal end of said outer housing when rotated in a second direction.

14. The multiple stapling anastomosis device of claim 4, further comprising an anvil closure sheath, said anvil closure sheath capable of being positioned over said at least one stapler anvil to place said at least one anvil bolster in communication with said vessel.

* * * * *